United States Patent
Sundheimer et al.

(10) Patent No.: US 7,950,869 B2
(45) Date of Patent: *May 31, 2011

(54) TUBE CONNECTION JOINT AND METHOD OF FORMING SAME

(75) Inventors: Herbert Alan Sundheimer, Ellettsville, IN (US); Christopher A. Benning, Ellettsville, IN (US); Changqing Li, Ellettsville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 961 days.

This patent is subject to a terminal disclaimer.

(21) Appl. No.: 11/565,568

(22) Filed: Nov. 30, 2006

(65) Prior Publication Data

US 2007/0140786 A1   Jun. 21, 2007

Related U.S. Application Data

(63) Continuation of application No. 10/946,992, filed on Sep. 21, 2004, now Pat. No. 7,165,910, which is a continuation of application No. 10/354,249, filed on Jan. 28, 2003, now abandoned.

(51) Int. Cl.
*F16B 7/00* (2006.01)
(52) U.S. Cl. .......................... 403/292; 403/288; 403/298
(58) Field of Classification Search .................. 403/167, 403/168, 272, 286–288, 291–298, 310, 387; 277/316, 641, 650, 910; 606/61, 69, 70, 606/71, 72
See application file for complete search history.

(56) References Cited

U.S. PATENT DOCUMENTS

| | | |
|---|---|---|
| 3,406,979 A | 10/1968 | Weber |
| 3,687,493 A | 8/1972 | Lock |
| 3,879,071 A | 4/1975 | Gockler |
| 4,041,599 A | 8/1977 | Smith |
| 4,224,163 A | 9/1980 | Goldhaber |
| 4,268,041 A | 5/1981 | Sovish |
| 4,352,584 A | 10/1982 | Smith |
| 4,511,163 A | 4/1985 | Harris |
| 4,660,867 A | 4/1987 | Kemper |
| 4,681,477 A | 7/1987 | Fischer |
| 4,718,404 A | 1/1988 | Sadler |
| 4,867,133 A | 9/1989 | Sadler |
| 5,078,362 A | 1/1992 | Lawless |
| 5,094,463 A | 3/1992 | Dryden |

(Continued)

FOREIGN PATENT DOCUMENTS

DE    1158779    12/1963

(Continued)

OTHER PUBLICATIONS

"Silicone Adhesive Sealant Product Description," <http://www.nwbuildnet.com/stores/bm/ada/vandu/txt/silicon.txt> [retrieved Dec. 1, 2005].

*Primary Examiner* — Victor MacArthur
(74) *Attorney, Agent, or Firm* — Kenyon & Kenyon LLP

(57) ABSTRACT

A connection joint (20) is described that is formed by inserting a plastic connector (10) into the end of a silicone tube (14). The connector includes a plurality of barbs (12). A reinforcing agent (16) is placed between each of the barbs (12) of the connector (10). An adhesive (18) is injected between the tube (14), the reinforcing agents (16) and the connector (10). The adhesive (18) is then cured at a predetermined temperature for a predetermined time in order to solidify the connection joint (20).

3 Claims, 2 Drawing Sheets

U.S. PATENT DOCUMENTS

| | | |
|---|---|---|
| 5,147,916 A | 9/1992 | Sweet |
| 5,265,890 A | 11/1993 | Balsells |
| 5,280,927 A | 1/1994 | Greisinger |
| 5,294,133 A | 3/1994 | Dutta |
| 5,516,117 A | 5/1996 | Rangel |
| 5,743,327 A | 4/1998 | Villa |
| 5,770,139 A | 6/1998 | Kinghorn |
| 5,772,551 A | 6/1998 | Mabie |
| 5,880,210 A | 3/1999 | Schulz |
| 5,912,433 A | 6/1999 | Pulido |
| 5,913,852 A | 6/1999 | Magram |
| 6,059,632 A | 5/2000 | Sassak |
| 6,454,097 B1 | 9/2002 | Blanco |
| 6,616,370 B1 | 9/2003 | Signorelli |
| 2002/0148058 A1 | 10/2002 | Greenwood |

FOREIGN PATENT DOCUMENTS

| | | |
|---|---|---|
| DE | 4202228 A1 | 7/1993 |
| EP | 0450330 A1 | 10/1991 |

TUBE CONNECTION JOINT AND METHOD OF FORMING SAME

CROSS-REFERENCE TO RELATED APPLICATIONS

This application is a continuation of U.S. application Ser. No. 10/946,992, filed Sep. 21, 2004, now U.S. Pat. No. 7,165,910, which is a continuation of U.S. application Ser. No. 10/354,249, filed Jan. 28, 2003, now abandoned, entitled TUBE CONNECTION JOINT AND METHOD OF FORMING SAME, the disclosure of which is hereby expressly incorporated by reference and the priority from the filing date of which is hereby claimed under 35 U.S.C. §120.

FIELD OF THE INVENTION

The present invention relates to a connection joint formed between a tube and connector, and more particularly to a connection joint formed between a silicone tube and a plastic connector.

BACKGROUND OF THE INVENTION

A large number and variety of medical devices use silicone tubing to deliver fluids and gases to patients. Often, these silicone tubes must be connected to another component of the medical device in order to serve its intended purpose. For example, in an enteral feeding delivery system, a silicone tube is used to deliver nutritional and other fluids to a patient through the stomach wall. The silicone tube is coupled via a plastic connector to a dialator which facilitates the insertion of the silicone tube through an incision in the stomach. In order to properly insert the dialator and position the silicone tube, the physician is often required to pull on the silicone tube. The connection joint between the silicone tube and the dialator must be able to withstand such forces in order to avoid physical injury to the patient or malfunction of the device. Unfortunately, silicone does not bond particularly well to other materials, such as plastic, which is commonly used in medical devices. Consequently, such connection joints separate at an unacceptable rate. Accordingly, a connection joint is needed that creates a bond with silicone having a sufficient tensile strength to withstand the pulling forces commonly experienced in medical or other applications.

SUMMARY OF THE INVENTION

In accordance with the present invention, a connection joint is provided having increased tensile strength. The connection joint is formed from a connector having a plurality of barbs inserted into a tube. To further reinforce this connection, a reinforcing agent is placed between at least one pair of the barbs and an adhesive is injected between the tube, the connector and the reinforcing agent. The adhesive is then cured at a predetermined temperature for a predetermined time in order to solidify the connection joint.

In accordance with yet other aspects of the present invention, the durometer of the reinforcing agent is greater than or equal to about that of the adhesive injected between the tube, the connector and the reinforcing agent. In one embodiment, the reinforcing agent is of a durometer greater than about 70 shore A, while the durometer of the adhesive is less than about 60 shore A. Although the reinforcing agent may take a variety of forms, in one embodiment of the present invention, the reinforcing agent comprises an O-ring. In another embodiment the reinforcing agent comprises a plurality of particles suspended in the adhesive injected between the tube, the connector and the reinforcing agent.

In accordance with yet other aspects of the present invention, the reinforcing agent may be placed between at least one pair of barbs in the connector, between more than one pair of barbs in the connector or between each pair of barbs in the connector. In yet other embodiments, the connection joint may be formed between a female receptacle (i.e., not necessarily a tube) and male connector. The male connector may include at least one groove defined therein, into which the reinforcing agent is placed and the adhesive is injected. Finally, in yet other embodiments of the present invention, a method for forming the connection joint described above is provided.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PRESENT INVENTION

Figure 1:
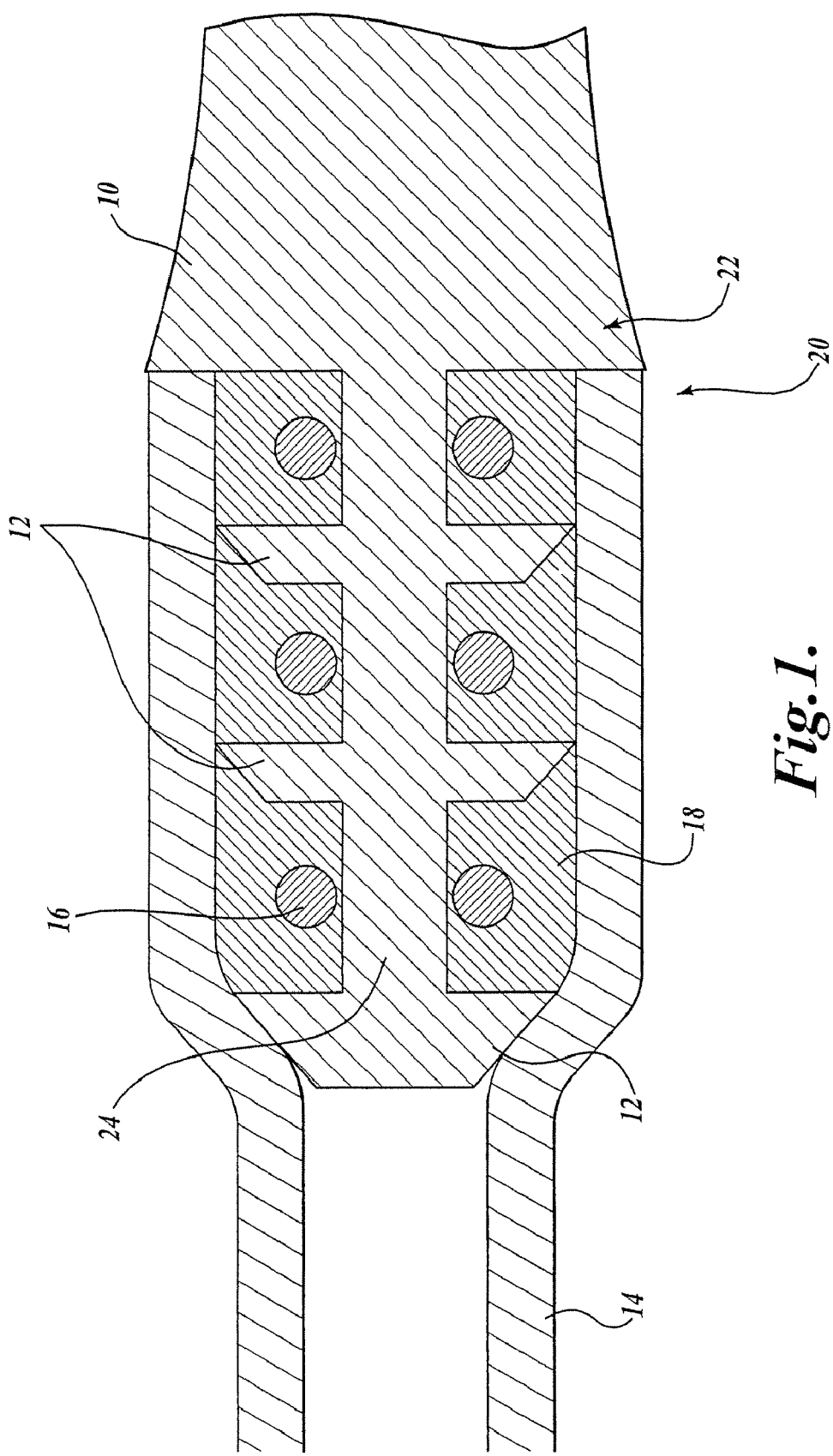
FIG. 1 is a cross-section view of a connection joint formed in accordance with the present invention.

FIG. 1 illustrates a connection joint 20 formed in accordance with the present invention. The connection joint 20 is formed by inserting a plastic connector 10 into the open end of a silicone tube 14. The connector 10 comprises a first end 22 and an arm 24 protruding therefrom. A plurality of barbs 12 extend radially from the arm 24. In the illustrated embodiment, the connector 10 includes three barbs. However, those skilled in the art will appreciate that the connector 10 may include any number of barbs 12 deemed suitable for establishing a sufficient connection joint 20. Accordingly, the connector 10 may include as little as one barb. Prior to inserting the connector 10 into the open end of the tube 14, a reinforcing agent 16, non-homogenuously formed with the connector, is placed between each of the barbs 12 of the connector 10, as well as between the first end 22 of the connector 10 and the barb 12 closest to it. In the embodiment of the present invention illustrated in FIGS. 1 and 2, the reinforcing agent 16 is an O-ring placed between the barbs 12 of the connector 10. Once the reinforcing agents 16 and the barbs 12 of the connector 10 have been inserted in the open end of the tube 14 (or, stated another way, once the tube 14 has been pushed over the reinforcing agents 16 and barbs 12 of the connector 10), an adhesive 18 is injected between the tube 14, the reinforcing agents 16, and the connector 10. More specifically, the adhesive 18 is injected in the spaces left between the barbs 12, the reinforcing agent 16, and the tube 14. The adhesive 18 is then cured at a predetermined temperature for a predetermined time, as will be described in more detail below, in order to solidify the connection joint 20.

In one embodiment of the present invention, the adhesive injected between the tube 14, the reinforcing agents 16 and the connector 10 is a silicone adhesive that, when cured, solidifies into a silicone rubber. A silicone adhesive with a higher durometer is used in an effort to further increase the tensile strength of the connection joint 20. In one embodiment of the present invention, the silicone adhesive 18 is of a durometer of greater than about 40 shore A and less than about 60 shore A. Once the silicone adhesive 18 is injected into the connection joint 20 it is cured at a predetermined temperature for a predetermined duration of time. As those skilled in the art shall appreciate, the lower the curing temperature is, the longer the curing time required and vice versa.

In one embodiment, the minimum practical curing temperature is as low as room temperature (although lower curing temperatures are theoretically possible), while the maximum curing temperature is limited by the melting point of the plastic of the connector 10. Further, the curing time is of a duration necessary to ensure sufficient rubberization of the silicone adhesive 18. In one embodiment of the present invention, the connector 10 is made of high-density polyethelene having a melting point of 200° F. Accordingly, the silicone adhesive 18 is cured for approximately three hours at 190° F. This temperature is lower than the melting temperature of the plastic connector 10, yet high enough to produce a relatively short curing time. Although theoretically, a curing time as low as eleven minutes could be used at a curing temperature of 190° F., additional curing time is used in order to fully ensure sufficient rubberization of the silicone adhesive in accordance with manufacturing requirements. Those skilled in the art will recognize, however, that the curing times and temperatures may vary depending on the type of plastic used for the connector 10, the type or durometer of the silicone adhesive 18 used and the manufacturing requirements present. Further, those skilled in the art will appreciate the other types or compositions of adhesives may be used without departing from the spirit and scope of the present invention.

Although silicone adhesive 18 does bond or adhere to the tube 14 and the connector, the present invention further strengthens that bond. More specifically, it has been discovered that the greater the durometer of the silicone between the barbs 12 of the connector 10, the greater the tensile strength of the connection joint 20, i.e., the greater pulling force the connection joint 20 can withstand without separating. However, there is often an upper limit to the durometer of silicone adhesive that can be injected due to manufacturing requirements, type of silicone adhesive used, cost, etc. Accordingly, to increase the durometer of the silicone between the tube 14 and connector 10, a reinforcing agent 16 having a durometer greater than or equal to the silicone adhesive 18 is placed between the barbs 12. The reinforcing agent 16 reinforces the adhesive 18 which surrounds it, creating a stronger bond between the connector 10 and the tube 14 than the adhesive 18 would have formed alone. Accordingly, the tensile strength of the connection joint 20 is increased. Use of such a reinforcing agent has advantages over other techniques for reinforcing the bond of the connection joint such as adding heat shrink to the outside diameter of the tube 14 or tying a suture around the outside diameter of the tube 14 between the barbs 12.

Figure 2:
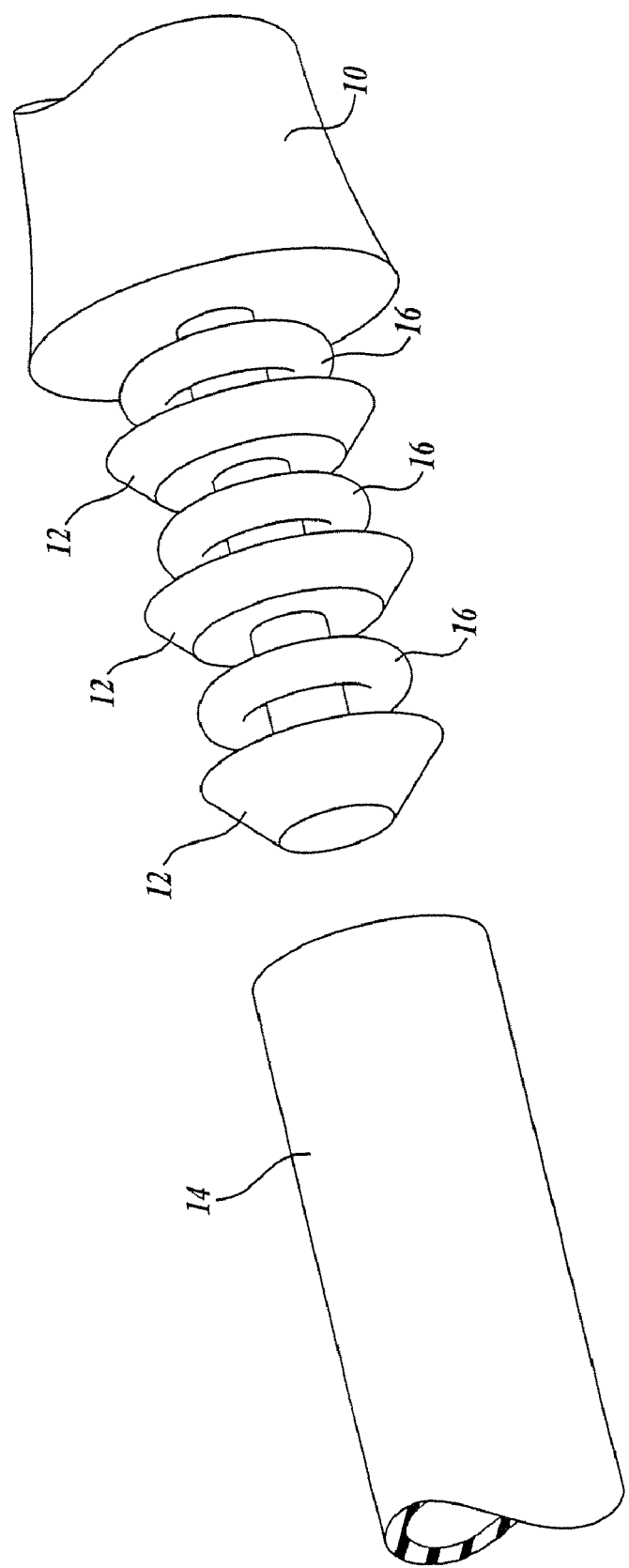
FIG. 2 is a perspective, exploded view of the connection joint shown in FIG. 1.

In the embodiment of the connection joint 20 depicted in FIGS. 1 and 2, the reinforcing agent 16 is an O-ring that neither continuously contacts the inner surface of the tube 14 nor the outer surface of the arm 24. Such O-ring is made of silicone and having a durometer greater than about 70 shore A and less than about 90 shore A. However, as noted above, the reinforcing agent 16, e.g., an O-ring, may be of any durometer greater than or equal to about that of the surrounding adhesive 18. Those skilled in the art will also appreciate that the reinforcing agent 16 may take a variety of different forms and be made of a variety of different materials without departing from the spirit and scope of the present invention. For example, the reinforcing agent 16 may take the form of silicone particles or polymeric bodies suspended in the adhesive 18. Said particles or bodies can be injected along with the adhesive 18 between the tube 14 and connector 10, or they can be placed between the tube 14 and the connector 10 prior to injecting the adhesive. Said reinforcing agent 16 can be made of silicone or of any other material suitable for reinforcing the bond between the connector 10 and the tube 14, such as metal. In addition, those skilled in the art will appreciate that the reinforcing agent 16 may comprise a ring having an "O" shape or any other shape suitable for either fully or partially surrounding the arm 24 of the connector 10 between the barbs 12. Those skilled in the art will also appreciate that in other embodiments of the present invention, different types of reinforcing agents 16 may be placed between the barbs 12 of the connector 10. For example, an O-ring may be used between one pair of barbs while particles may be suspended between others. In yet other embodiments, an O-ring may be used along with other particles between the same pair of barbs 12. Finally, it will be appreciated that in some embodiments, a reinforcing agent 16 is not placed between each pair of barbs 12 of the connector 10.

While certain embodiments of the invention have been illustrated and described, those skilled in the art will appreciate that various changes can be made without departing from the spirit and scope of the invention. For example, the connector 10 may be made of any material, e.g., plastic, metal, etc., deemed suitable for the particular application of the connection joint 20. In one embodiment of the present invention, the connector 10 is made of high-density polyethylene, which does not impact the curing reaction of the silicone adhesive 18. In yet other embodiments of the present invention, the connection joint 20 may be formed between a female receptacle (i.e., not necessarily a tube 14) and a male connector 10. The male connector 10 may include at least one groove defined therein, e.g., the space defined between a pair of barbs, into which a reinforcing agent 16 is placed and an adhesive 18 is injected. Finally it will be appreciated that either the female receptacle or the male connector may be made of plastic while the other is made of silicone.

The embodiments of the invention in which an exclusive property or privilege is claimed are defined as follows:

1. A connection joint comprising:
   a female receptacle;
   a male connector having at least one groove defined therein, the male connector at least partially disposed in the female receptacle, wherein one of the female receptacle and the male connector is made of plastic and the other is made of silicone;
   a reinforcing agent disposed in the groove; and
   a silicone adhesive disposed in the groove, surrounding the reinforcing agent and adhered to the male connector and the female receptacle.

2. A connection joint comprising:
   a tube;
   a connector having a plurality of barbs disposed in the tube;
   a reinforcing agent disposed between at least one pair of the barbs, wherein the reinforcing agent is non-integrally formed with the connector; and
   an adhesive disposed between the tube, the connector and the reinforcing agent, the adhesive being adhered to the connector and the tube.

3. A connection joint comprising:
   a tube;
   a connector disposed in the tube, the connector having a first end and a barb spaced apart from the first end;
   a reinforcing agent disposed between the barb and the first end of the connector, wherein the reinforcing agent is non-integrally formed with the connector; and
   an adhesive disposed between the tube, the connector, and the reinforcing agent, the adhesive being adhered to the connector and the tube.

* * * * *